United States Patent

Rastopov et al.

[11] Patent Number: 5,846,759
[45] Date of Patent: Dec. 8, 1998

[54] METHOD OF DETECTING LIVE MICROORGANISMS

[75] Inventors: Stanislav Fedorovich Rastopov, Moscow; Vladimir Gennadievich Ageev, Moscow, both of Russian Federation

[73] Assignee: Rusteck Limited, St. Helier, Channel Islands

[21] Appl. No.: 894,044

[22] PCT Filed: Oct. 14, 1996

[86] PCT No.: PCT/RU96/00299

§ 371 Date: Nov. 3, 1997

§ 102(e) Date: Nov. 3, 1997

[87] PCT Pub. No.: WO97/21799

PCT Pub. Date: Jun. 19, 1997

[30] Foreign Application Priority Data

Dec. 9, 1995 [RU] Russian Federation ........... 951202364

[51] Int. Cl.[6] ................ C12Q 1/02; C12Q 1/04; C12Q 1/00

[52] U.S. Cl. ............ 435/29; 435/34; 435/4; 430/945

[58] Field of Search ............ 435/29, 34, 4; 430/945

[56] References Cited

U.S. PATENT DOCUMENTS

| 4,368,047 | 1/1983 | Andrade et al. | 435/34 |
| 4,467,032 | 8/1984 | Lowke et al. | 435/29 |
| 5,371,016 | 12/1994 | Berndt | 430/945 |

Primary Examiner—Louise N. Leary

[57] ABSTRACT

The invention relates to the field of optical biosensors and facilitates detection of mobile microorganisms in a liquid with a high degree of sensitivity even in the presence of a large number of brownian particles. The method in essence involves measuring, within a frequency range restricted at the lower end, the mean amplitude of the fluctuation in intensity of laser radiation scattered by the particles in the liquid, this being proportional to both the concentration and mobility of the particles. The turbidity of the liquid, which is proportional only to the particle concentration, is also measured and the presence of mobile microorganisms is assessed by comparing the two signals.

3 Claims, 1 Drawing Sheet

METHOD OF DETECTING LIVE MICROORGANISMS

The invention relates to the field of biophysics, more specifically to optical biosensors.

At present, live microorganisms in liquids are recorded by observation using an optical microscope and methods of bioluminescence and selective staining. A general disadvantage of these methods is the low degree of automation of measurement.

Closer to the applicant's method is an optical method for detecting mobile microorganisms [1] (prototype) by measuring coefficients of diffusion of scattering centres. In this method laser radiation passes through the liquid being investigated and is scattered by the particles (brownian motion) and mobile microorganisms in the liquid, and the scattered radiation, interfering on an observation surface, forms a dynamic speckle-picture, whose Fourier-spectrum of fluctuation of intensity is recorded. Based on the half-width of this spectrum the diffusion coefficient is calculated, and using its value the presence of mobile microorganisms is assessed.

A disadvantage of this method is that in order to distinguish mobile microorganisms from brownian particles it is necessary to have a priori information about the sizes of the particles being studied, and this reduces the applicability of the method. For example, differentiating between spectrums does not work if there is low mobility of mobile microorganisms, or brownian particles of small size are present. In addition, it is necessary to measure the Fourier spectrum to a high degree of accuracy, and this makes it more difficult and more expensive to create instruments working in real time.

The proposed method makes it possible to overcome the disadvantages mentioned by measuring the mean intensity of fluctuation of the speckle-picture, in a frequency range restricted at the lower end, associated both with the concentration of brownian particles and with the mobility of microorganisms. At the same time, using the known method, measurement takes place of the investigated medium's turbidity, which is associated only with the concentration of brownian particles and mobile microorganisms and does not depend on the mobility of the mobile microorganisms. This makes it possible to distinguish, in the output signal, between the contribution made by the concentration of brownian particles and mobile microorganisms and the contribution associated with the mobility of the microorganisms. Restriction of the frequency range at the lower end makes it possible to reduce the contribution in the output signal from the brownian particle concentration, whose spectrum lies in the low-frequency field, and causes little change to the signal associated with the mobility of the microorganisms, lying in a higher-frequency field. This makes it possible to increase the sensitivity of the method when detecting weak signals from mobile microorganisms against the background of a strong signal from brownian particles. The proposed method is simpler since there is no need for information about particle sizes and there is no need to measure the Fourier spectrum.

BRIEF DESCRIPTION OF DRAWINGS

The method is illustrated by three diagrams.

DETAILED DESCRIPTION OF THE INVENTION

The method is implemented as follows.

Laser radiation, passing through the liquid being investigated, is scattered by the particles in the liquid, and, interfering on the surface of a photodetector, forms a dynamic speckle-picture. The amplitude-frequency spectrum of fluctuation of the photocurrent is a Lorentz line:

$$U = U_0 \frac{2\Delta\omega}{\omega^2 + (2\Delta\omega)^2} \quad (1)$$

where

U—voltage at photodetector, $U_0$—multiplier with dimensions of voltage, $\Delta\omega$—half-width of Lorentz line, $\omega$—present frequency, $\Delta\omega \sim D \cdot \sin^2\phi$, where $\phi$—angle of observation, D—coefficient of diffusion of scattering particles.

For brownian particles, D is inversely proportional to their radius r:

$$D \sim 1/r \quad (2)$$

while for mobile microorganisms D is proportional to the root from their velocity V:

$$D \sim \sqrt{V} \quad (3)$$

Figure 1:
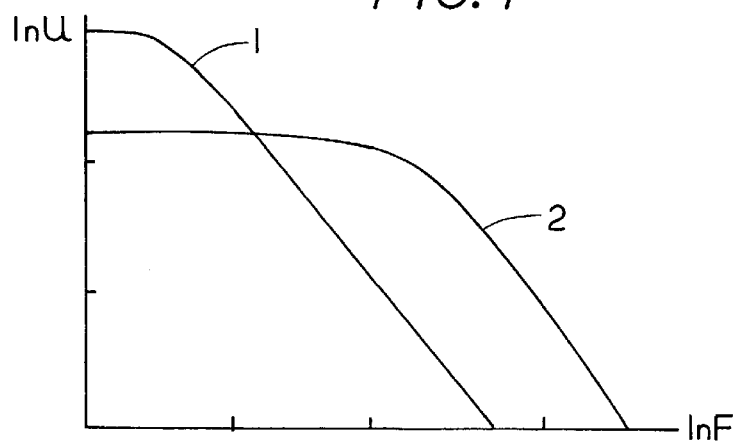
FIG. 1 shows typical amplitude-frequency spectrums of output signals, where 1—Fourier spectrum for brownian particles, 2—Fourier spectrum for mobile microorganisms.
Figure 2:
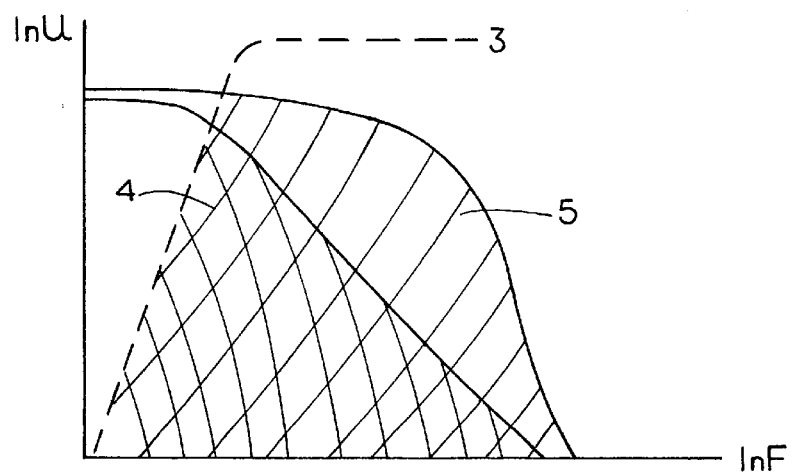
FIG. 2 shows integral values measured under the proposed method, where 3—amplitude-frequency characteristic curve for limiting the spectrum at the lower end, area 4—integral signal $U_1$ for brownian particles, area 5—integral signal $U_2$ for brownian particles plus mobile microorganisms.
Figure 3:
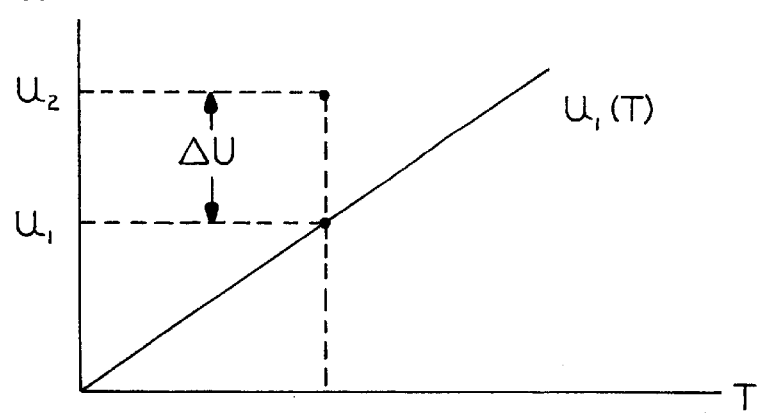
FIG. 3 shows the dependence of signal $U_1$ on turbidity of liquid T (solid line), where $\Delta U$ is the contribution to the output signal caused by mobility of microorganisms.

For mobile microorganisms D is larger than for brownian particles, making it possible to detect mobile microorganisms in the liquid. FIG. 1 shows Lorentz spectrums (1) for brownian particles 1 and mobile microorganisms with high mobility 2 on the assumption that their concentrations and sizes are identical. Here, the areas under the corresponding curves are identical, while U-∞ with ω-0 and Δω-0. If brownian particles and mobile microorganisms are present at the same time in the medium being investigated, the resulting spectrum is a superposition of the spectrums given in FIG. 1. When restricting the frequency spectrum of the measured signal at its lower end (curve 3 on FIG. 2) $U_{1(2)}$ the recorded integral intensity for the brownian particles is reduced far more strongly than for the mobile microorganisms (areas 4 and 5 respectively on FIG. 2), since the greater part of the brownian particle spectrum is positioned in the low-frequency area. The lower boundary frequency that was used near to a Δω typical for brownian particles about a micron in size and was 1–10 Hz. Its precise value is not a critical parameter. Here, U for the brownian particle spectrum is determined independently by measuring the turbidity of the medium. This is illustrated in FIG. 3, which shows the experimental dependence U(T), of the mean amplitude of fluctuation of the speckle-picture, on the turbidity of medium T when only brownian particles are present in it (solid line). Turbidity T was measured by a photodetector in terms of integral intensity of scattered light and also has dimensions of voltage. Then, if only brownian particles are present in the medium $$U_2 = K \cdot T \quad (4)$$

where K—coefficient of proportionality, constant for this implementation of the method. In an actual medium where both brownian particles and mobile microorganisms are present it is possible, in the signal U being measured, to distinguish the contribution made by the mobile microorganisms as the excess of U over (4):

$$U_{=}=U_1+\Delta U \quad (5)$$

The presence of $\Delta U$, and its value, are characteristic of the presence of mobile microorganisms and of their activity in the medium under investigation (see FIG. 3). The relative contribution of the signal from the mobile microorganisms may also be characterized by the ratio $\Delta U/U_2$.

The sensitivity of the proposed method is higher compared to the prototype, since it is possible to isolate a "clean" contribution from mobile microorganisms in the signal being recorded; in the prototype it is merely the total spectrum from brownian particles and mobile microorganisms that is recorded. In our experiments sensitivity $\Delta U/U_2$ was about 10%.

With the aim of detecting dynamic processes connected both with mobile and with non-self-mobile but living microorganisms (for example, processes of division), measurements were made of the first and higher derivatives $dU_{1(2)}/dt$, characterizing, for example, the speed of change of concentrations of living microorganisms.

Thus, the proposed method is practical and commercially usable.

LITERATURE

1. Spectroscopy of optical mixing and correlation of photons, ed. G. Kammins and E. Paik. M: "Mir", 1978, pp. 287–331.

We claim:

1. A method for detecting live microorganisms, comprising passing laser radiation through the sample being analyzed and measuring the parameter characterizing the amplitude-frequency spectrum of fluctuation of the scattered laser radiation in the sample, simultaneously measuring the parameter characterizing the turbidity of the sample, while measuring the parameter characterizing the amplitude-frequency spectrum of fluctuation of scattered laser radiation with a restriction on the lower limit of the frequency range, and detecting the presence of live microorganisms by comparing the measured parameters.

2. The method as claimed in claim 1, wherein the lower limit of the frequency range is set taking account of the half-width of the Lorentz line.

3. The method as claimed in claim 1, further comprising calculating the derivatives of the measured parameters.

* * * * *